US006256538B1

(12) United States Patent
Ekwall

(10) Patent No.: US 6,256,538 B1
(45) Date of Patent: Jul. 3, 2001

(54) IMPLANTABLE HEART STIMULATOR

(75) Inventor: Christer Ekwall, Spånga (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/341,941

(22) PCT Filed: Jan. 13, 1998

(86) PCT No.: PCT/SE98/00043

§ 371 Date: Sep. 22, 1999

§ 102(e) Date: Sep. 22, 1999

(87) PCT Pub. No.: WO98/31421

PCT Pub. Date: Jul. 23, 1998

(30) Foreign Application Priority Data

Jan. 22, 1997 (SE) ............ 9700182

(51) Int. Cl.[7] ............ A61N 1/365

(52) U.S. Cl. ............ 607/17

(58) Field of Search ............ 607/9, 10, 11, 607/12, 13, 14, 15, 16, 17, 18, 19, 20, 21, 22, 23, 24, 25, 26

(56) References Cited

U.S. PATENT DOCUMENTS 5,025,786 6/1991 Siegel .
5,199,428 4/1993 Obel et al. .
5,531,768 7/1996 Alferness .
6,021,350 * 2/2000 Mathson ............ 607/17

FOREIGN PATENT DOCUMENTS 0 721 786 7/1996 (EP) .

* cited by examiner

*Primary Examiner*—Scott M. Getzow
(74) *Attorney, Agent, or Firm*—Schiff Hardin & Waite

(57) ABSTRACT

An implantable heart stimulator has a control unit which controls the delivery of stimulation pulses to a subject, and an ischemia detector. The control unit is connected to the ischemia detector and reduces the stimulation rate in response to a detection of ischemia.

17 Claims, 3 Drawing Sheets

ELECTRODE
12
SENSOR
14
LEAD
10
HEART STIMULATOR
ECG APPARATUS
7
TELEMETRY UNIT
9
2
5
IEGM RECORD-ING UNIT
TELEMETRY UNIT
11
4
ISCHEMIA ANALYZER
ALERTING UNIT
13
CONTROL UNIT
6
PULSE GENERATOR
8
3

IMPLANTABLE HEART STIMULATOR

BACKGROUND OF THE INVENTION

1. Field of the Invention

The present invention relates to an implantable heart stimulator of the type having control means for controlling the delivery of stimulation pulses and an ischemia detector.

2. Description of the Prior Art

The aortic pressure is produced by the pumping action of the heart. During heart contraction—a systole—the blood pressure inside the heart is equal to or slightly higher than the pressure in the aorta, as long as the aortic valve is open and blood is flowing from the ventricle into the aorta or pulmonary artery. Between the contractions, that is during diastole, the aortic pressure is maintained by the elastic properties of the aortic wall. From the aorta, blood is circulated back to the heart via different parts of the body through the venous system. In this way blood is distributed to different organs of the body depending on the needs, the overall control of this distribution emanating from the autonomous nerve system.

Blood penetration of the heart is possible only in the diastolic phase when the aortic valve is closed. About 60% of the oxygen content inside the heart tissue is consumed during a heart contraction and in order to maintain the efficiency of the heart the consumed oxygen must be refilled till the next contraction.

The effect of an increased workload, due to e.g. movement of the patient, climbing stairs, running etc., is a higher blood flow in the body and a resulting increased need of energy and oxygen. This in its turn results in a more rapid decay of the aortic blood pressure between consecutive heart contractions. In response to such an increased demand a healthy heart is pumping at a higher rate and with an increased pumping force.

An increased heart rate results in only a minor shortening of the systolic phase, that is an increased heart rate results mainly in a shortening of the diastolic phase, which is the period during which oxygen is supplied to the heart as mentioned above.

An ischemic heart has a deficiency of oxygen because of insufficient blood to the heart tissue supply due to congestion and blocking of the coronary vessels by stenosis, emboli or spastic congestion. An increased workload will consequently worsen the situation for an ischemic patient.

In such a situation a symptomatic ischemia, that is angina pectoris, heart insufficiency or infarct, will force the patient, because of the associated pain, to stillness with a reduced heart rate as a consequence. This heart rate reduction can then at best stop the ischemic state.

No pacemaker system able to react on pain or any other ischemic indication is known. As a matter of fact pacemakers normally try to maintain a high stimulation rate, which is appropriate to a normal situation of the patient, and a so called rate response pacemaker system, responding to metabolical, haemodynamical or activity inputs will tend to increase the stimulation rate with increasing workload, thus worsening the ischemic situation of the patient.

In U.S. Pat. No. 5,199,428 a technique is described for detecting ischemia and both affecting stimulation of nerves regulating blood pressure and heart rate to reduce the heart'oxygen requirements while providing pacing therapies to maintain the patient's heart rate within acceptable limits, i.e. to overcome bradyarrhythmias and/or unphysiological AC-delays induced by the nerve stimulation.

SUMMARY OF THE INVENTION

An object of the present invention is to provide a heart stimulator which can be used for therapeutic treatment of an ischemic state of a living subject.

This object is achieved in accordance with the principles of the present invention in an implantable heart stimulator having control means for controlling the delivery of stimulation pulses, and an ischemia detector, wherein the control means are connected to the ischemia detector for reducing the stimulation rate in response to a detected ischemia.

Depending on which kind of ischemia detector is used it is possible to detect an ischemia even before the patient gets any symptoms and thus by therapy prevent the occurrence of symptoms.

In the invention there are different ways of reducing the stimulation rate. According to one embodiment of the stimulator according to the invention the control means inhibit each with stimulation pulse in response to the detection of an ischemia, where n=8, . . . , 2. The resulting prolonged interval between two consecutive stimulation pulses will mimic the situation in normal heart operation where it frequently occurs that one heart beat is suppressed, possibly because of e.g. sudden, pressure changes, low oxygen or low glucose concentrations, and this prolonged interval will improve the supply of oxygen to the heart tissue and improve the possibility of terminating the ischemic state. In addition the prolonged interval will result in an increased blood filling of the heart ventricles, which in its turn will increase the efficiency of the next heart beat and compensate for any drop in the aortic pressure and reduction in blood filling because of the suppressed heart beat. The frequency of suppressed stimulation pulses can be varied depending on the degree of ischemia. To start with e.g. one stimulation pulse out of eight can be inhibited. At an increased degree of ischemia, or sustained ischemia over a period of time despite these suppressed stimulation pulses, one out of four pulses, or one out of two pulses can be suppressed. In the last mentioned example the stimulation rate is halved and the length of the diastolic phase, in which part oxygenic change takes place, is more than doubled, of, the discussion above. According to other advantageous embodiments of the heart stimulator according to the invention said control means are arranged to uniformly reduce the stimulation rate or shift the stimulation rate to a predetermined lower value in response to the detection of an ischemia.

In another embodiment of the heart stimulator according to the invention the control means are arranged to reduce the stimulation rate as a function of the detected degree of ischemia. In the case of a fully developed ischemia the stimulation rate is permitted to drop to a set predetermined minimum rate.

In another embodiment of the heart stimulator according to the invention, the heart stimulator is a rate response controlled rate responsive pacemaker, the control means are arranged to shift the stimulation rate to a base rate below the normal rate response controlled stimulation rate.

In another embodiment of the heart stimulator according to the invention said ischemia detector comprises ischemia analyzing means for detecting an ischemia by analysis of recorded IEGMs or ECGs. In an implantable heart stimulator it is suitable to determine an ischemia by analyzing ECGs since the lead for recording the IEGMs already is in place and the technique for IECG sensing is well established and no special sensors are needed. Body surface ECG diagnostics for determining ischemic states also are well known.

In a further embodiment of the heart stimulator according to the invention the ischemia analyzing means detect an ischemia by analysis of the level of ST-segments and T-wave forms of recorded IEGMs or ECGs. The level of ST-segments and the appearance of T-wave forms are related to repolarization of groups of cells, and the repolarization after a heart contraction is sensitive to haemodynamics, like fuel and oxygen supply.

In a further embodiment of the heart stimulator according to the invention the ischemia analyzing means determine heart rate variability from recorded IEGMs or ECGs. Normally heart beat intervals, AV-conduction intervals and QRS-amplitudes are subject to variations. Heart rate variation is at a maximum for a healthy individual at rest. Activity of the individual or reduction in capacity due to insufficiency or illness is reflected as a decrease in the heart rate variability and this effect is used for ischemia detection.

In a further embodiment of the heart stimulator according to the invention the control means modulate the stimulation rate. During stimulation underlying spontaneous cardiac activities can often not be observed. However, e.g. elevation of the ST-segment as indicator of a beginning ischemia can be made observable by stimulation rate modulation.

It is known that the heart wall is thickening and stiffening as a result of an ischemia. The accompanying change in the moving pattern of the heart well can be detected by measuring different parameters and used for detection of an ischemic situation. Thus, according to another embodiment of the heart stimulator according to the invention, the ischemia detector has a lead bending sensor located at the distal end portion of the lead. With such a sensor the reduced ability of the ventricles to contract and expand can be detected as an indication of an ischemia. Alternatively, the ischemia detector can include means for measuring the AC-impedance in the ventricle. The magnitude of the AC-impedance is a measure of the blood filling of the ventricle and consequently such an impedance measurement can be used for detecting an ischemic situation.

In an alternative embodiment of the heart stimulator according to the invention the ischemia detector includes means for measuring sound absorption in the heart tissue. The sound absorption is affected by changes in the stiffness of the heart tissue and the sound absorption measuring means can be provided to determine e.g. the absorption of sound waves generated at the valve closure on their way from the upper portion of the ventricle to the apex region.

Since ischemia represents a deterioration of the efficiency of the heart pumping, an ischemic situation can be detected by studying blood pressures and cardiac outputs. Thus, in another embodiment of the invention the ischemia detector includes means for measuring the difference between systolic and diastolic pressures and comparing this difference obtained from one heartbeat to the difference obtained from the next heartbeat.

In another embodiment of the heart stimulator according to the invention the ischemia detector includes a flow sensor to determine cardiac output.

In a further embodiment of the heart stimulator according to the invention alerting means are activated by the ischemia detector or by the control means in response to a detected occurrence of ischemia for alerting the patient. This is of value to patients having a "silent ischemia", the occurrence of which the patient otherwise would not be aware. When being alerted the patient may also suitably temporarily lower his or her activity.

DESCRIPTION OF THE PREFERRED EMBODIMENTS

Figure 1:
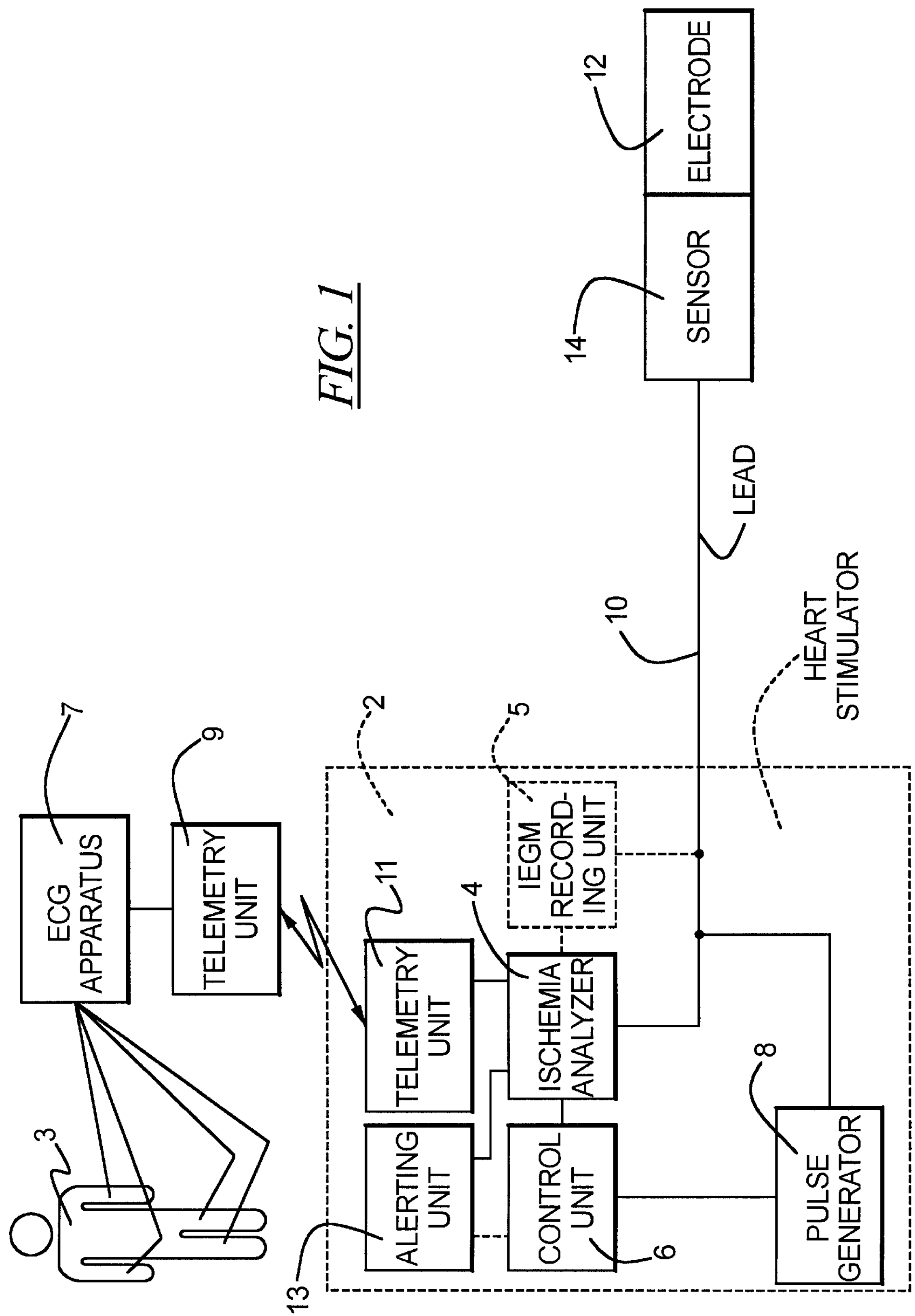
FIG. 1 is a schematic block diagram of a heart stimulator constructed and operating in accordance with the principles of the present invention.

FIG. 1 is a simplified block diagram of an implantable heart stimulator 2 according to the invention. The heart stimulator 2 contains an ischemia analyzer 4 and control unit 6, connected to the ischemia analyzer 4. The control unit 6 are connected to a pulse generator 8 for controlling the rate of generated stimulation pulses. The pulse generator 8 in its turn is connected to a lead 10 provided with electrodes 12 at the distal end portion for delivery of stimulation pulses and possible electrical measurements, which lead 10 is intended to be implanted into the heart of a patient, preferably with the electrodes in the right ventricle, of, FIG. 2. A sensor 14 which emits an electrical signal used for ischemia detection is also provided at the distal end portion of the lead 10 and the detected signals are supplied to the ischemia analyzer 4 through the lead 10, as well.

As will be described more in detail below an ischemic state can be detected by IEGMs and ECGs. For recording IEGMs the sensor 14 has electrodes as described in connection with FIG. 2 and the signals are supplied by the lead 10 to an IEGM recording unit 5 which in its turn is connected to the ischemia analyzer 4 for further analysis of the IEGMs. For recording surface ECGs on a patient 3 an ECG apparatus 7 is used and recorded electrocardiograms are transmitted by telemetry units 9 and 11 to the ischemia analyzer 4.

The heart stimulator is also provided with alerting unit 13, e.g. of a wristwatch "beeper-type". This alerting unit 13 is connected to the ischemia analyzer 4 to be activated by a detected ischemia.

Alternatively the alerting unit 13 can be connected to the control unit 6 to be activated when the stimulation rate is lowered. This is of value for patients having a "silent ischemia" the occurrence which the patient otherwise would not be aware of.

Figure 2:
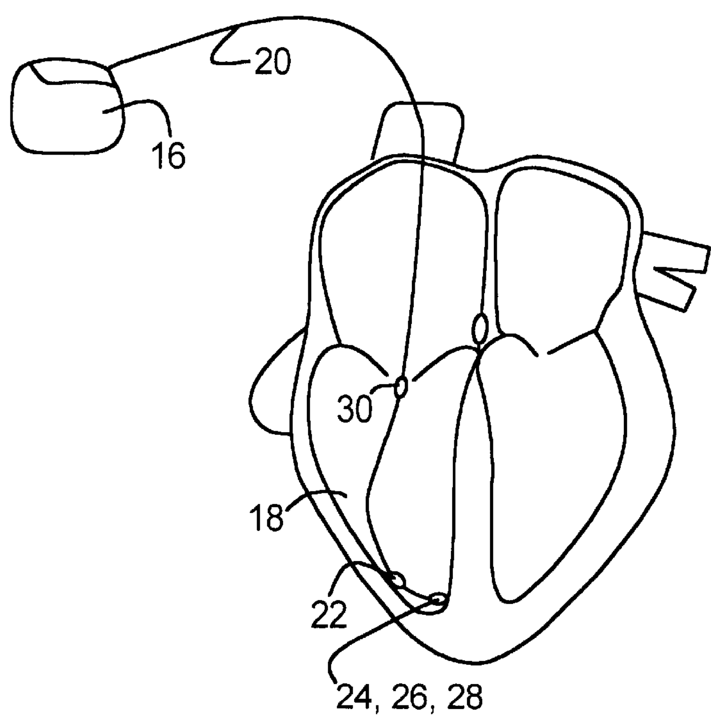
FIG. 2 shows a pacemaker constructed according to the diagram of FIG. 1, having a lead implanted in the right ventricle, the lead carrying stimulation electrodes and a sensor for the ischemia detector.

FIG. 2 shows an implanted heart stimulator in the form of a pacemaker 16, connected to the right ventricle 18 of the heart of a patient by its lead 20. The electrode lead 20 is a bipolar type with an electrode ring 22 and with a tip electrode 24 and a pressure sensor 20 provided at the distal end portion of the lead 20.

Figure 3:
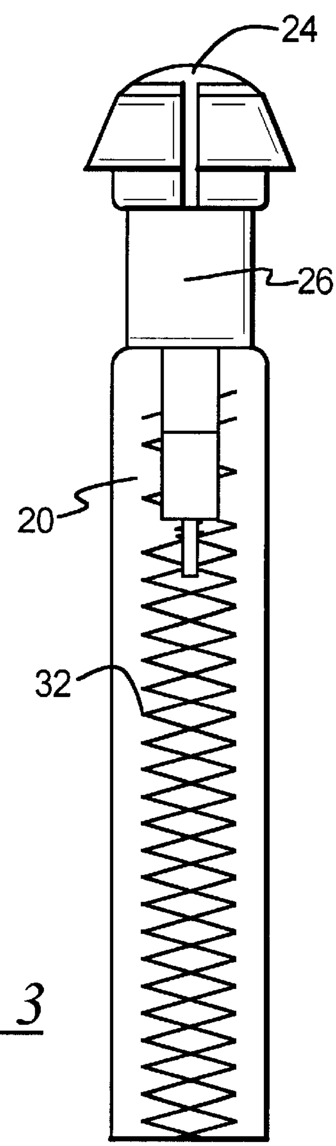
FIG. 3 is an enlarged longitudinal sectional view of the distal end of the lead of FIG. 2.

FIG. 3 shows the distal end portion of the electrode lead 20 in FIG. 2 on an enlarged scale in longitudinal cross section. The sensor 26 is placed just behind the tip electrode 24. The pressure sensor 26 is formed by a stiff cylindrical device of a piezo-electric material. Cloture and overgrowth will then not affect the sensing properties of a sensor 26. A helical conductor 32 inside the lead 20 connects the electrode 24 to the electronics in the pacemaker 16, cf. FIG. 2.

With the heart stimulator according to the invention the stimulation rate is reduced in response to the detection of ischemia. There are different possibilities of reducing the stimulation rate. The control unit 6 can inhibit the delivery of a particular stimulation pulse thus temporarily producing a longer interval between two consecutive pulses. The control unit 6 can also be arranged to more regularly inhibit a stimulation pulse out of a specified number of stimulation pulses in response to detected ischemia. The resulting prolonged interval between two consecutive stimulation pulses will then mimic the situation for a normal healthy heart where one heart beat is suppressed because of e.g. sudden blood pressure changes, low oxygen or glucose concentrations. The prolonged interval between two consecutive stimulation pulses will improve oxygen supply to the heart tissue and increase the probability to end the ischemic situation, as discussed above. In addition the prolonged interval will result in an increased blood filling of the heart ventricles, which will increase the efficiency of the next heartbeat and compensate for any drop in the aortic pressure or blood filling from the suppressed heartbeat.

The prolonged interval is, by healthy individuals, often referred to as "My heart is jumping". In the ischemic patient this "jumping" serves the purpose of an early indicator of ischemia. The patient may temporarily lower his/her activity to reduce the heart-rate and improve the oxygen supply.

The frequency of the suppressed stimulation pulses can be selected depending on the degree of the ischemia. Thus, initially 1 stimulation pulse out of 8 can be inhibited. Upon detection of an enhanced degree of ischemia, or sustained ischemia over a certain period of time despite this therapy, the frequency can be increased to 1 out of 4 or 1 out of 2 pulses. In the last situation the stimulation is halved and the diastolic period, during which oxygen is supplied to heart tissue, is more than doubled, which will give a good possibility to cure the ischemia.

As an alternative the control unit 6 can be arranged to control the pulse generator 8 such that the stimulation rate is uniformly reduced on the detection of an ischemia, or the stimulation rate can be shifted to a selected lower rate, or, in a more refined implementation, said control unit 6 can control the pulse generator 8 such that the stimulation rate is reduced as a function of the detected degree of ischemia.

Figure 4:
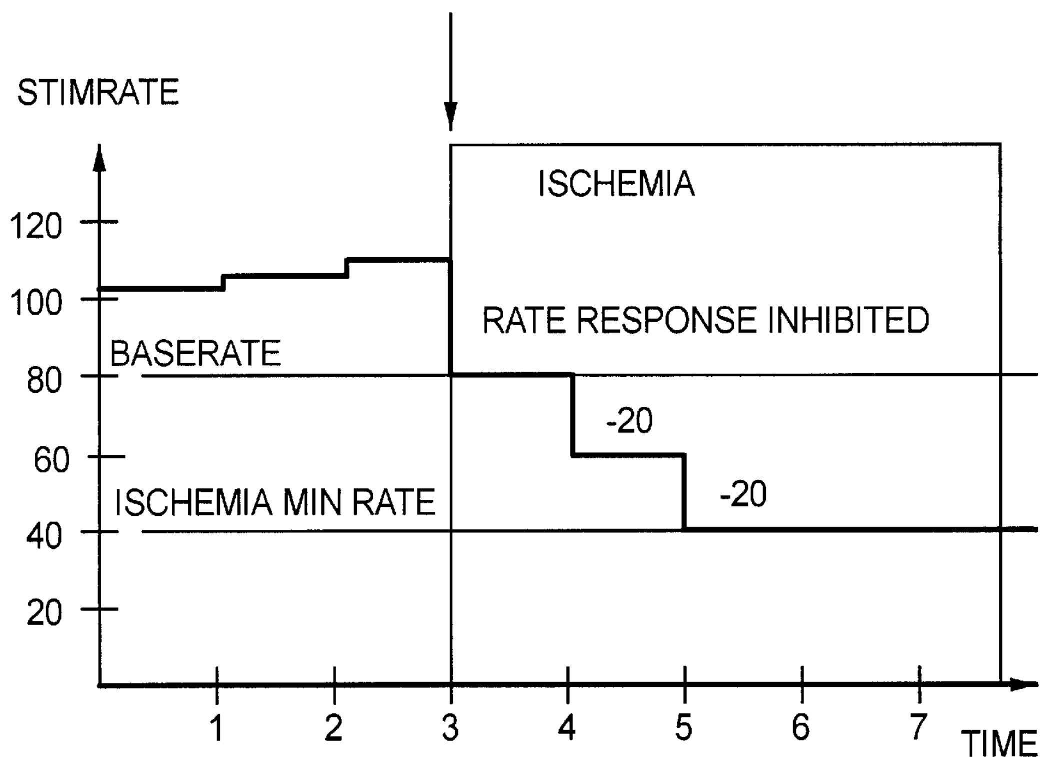
FIG. 4 is a diagram illustrating ischemia therapy which can be administered using the heart stimulator in accordance with the invention.

The regulation of the stimulation rate of the heart stimulator when an ischemia is detected is illustrated in FIG. 4, which shows the stimulation rate in pulses per minute versus time in an arbitrary scale. Thus in the interval 1–3 the heart stimulator is in a rate response mode of operation. At time 3 an ischemia is detected and the rate response function of the heart stimulator is inhibited and the stimulation rate is lowered to a base rate. At time 4 the stimulation rate is further lowered with 20 pulses per minute to try to cure the ischemic state of the patient, and at time 5 the stimulation is lowered with another 20 pulses per minute, an ischemia minimum rate then being reached.

For the detection of an ischemia different techniques can be used. For an implantable heart stimulator analysis of recorded IEGM is a suitable method for ischemia detection. The electrodes 22, 24 of the already implanted electrode lead 20, cf. FIG. 2, can then be used for the recordal of the IEGM. Also surface ECGs can be used for detection of an ischemic state. The recorded ECG's are then transmitted telemetrically to the ischemia analyzer 4, by telemetry unit 9 and 11 as described in connection with FIG. 1. An ischemia can then suitably be detected by analyzing the level of ST-segments or by analyzing alterations in the T-wave forms.

During stimulation underlying spontaneous heart activity cannot be observed. In this case a temporary increase in the stimulation rate can make changes in an observed parameter related to this spontaneous activity detectable. Thus by having the control unit 6 to modulate the pulse rate from the pulse generator 8 e.g. the elevation of ST-segments can be observed as an indicator of a beginning ischemia.

Figure 5:
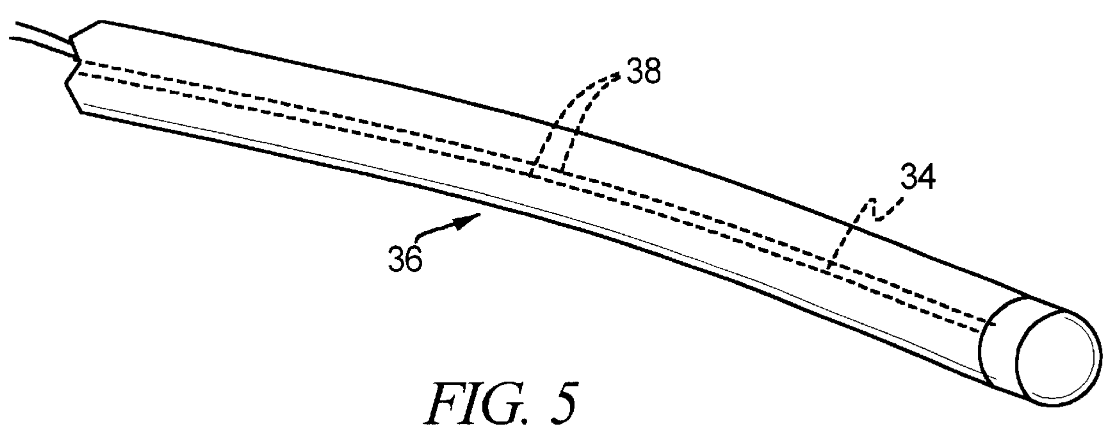
FIG. 5 illustrates a lead bending sensor for the ischemia detector in the heart stimulator of the invention.

It is known that the heart wall is thickening and stiffening as a result of an ischemia. Thus an ischemic situation can be detected by studying changes in the moving pattern of the heart wall. In FIG. 5 a lead bending sensor 34 is shown located at the distal end portion of a lead 36. This bending sensor 34 can include e.g. piezo-electric material which generates an electric signal when subject to bending movements, these signals being supplied to the ischemia analyzer 4, see FIG. 1, through conductors 38.

Ischemia can also be detected by AC-impedance measurements in the ventricle 18, as this impedance is related to the blood filling of the ventricle. For this impedance measurement the electrodes 22,24 of the lead 20, see FIG. 2, can be used and the measurement signals are supplied to the ischemia analyzer 4 through the conductors of the lead 20.

Further, ischemia can be detected from the sound absorption in the heart tissue, as this absorption is changed with changes in the stiffness of the heart tissue. Thus one microphone 28 is mounted at the distal end of the lead 20 and another microphone 30 is mounted on the lead 20 such that it will be positioned in the upper part of the ventricle 18 after implantation of the lead 20. In this way it is possible to measure the absorption of sound waves closure during propagation through the ventricle down to the microphone 28 situated at the ventricular bottom, see FIG. 2. The signals picked up by the microphones 28, 30 are fed to the ischemia analyzer 4 for analysis.

Ischemia can be detected by studying blood pressures and cardiac outputs as well, since ischemia will affect the efficiency of the heart pumping. Thus ischemia can be determined by measuring the difference between the systolic and the diastolic pressures and compare this difference from one heartbeat. Ischemia can also be detected by monitoring the systolic pressure over time. For these pressure measurements the pressure sensor 26 shown in FIG. 3 is used. The pressure signals obtained from the pressure sensor 26 is supplied through the lead 20 to the ischemia analyzer 4.

Cardiac output can be measured with a flow sensor positioned e.g. in the pulmonary artery.

Although modifications and changes may be suggested by those skilled in the art, it is the intention of the inventor to embody within the patent warranted hereon all changes and modifications as reasonably and properly come within the scope of his contribution to the art, including combining one or more of the above-identified techniques for ischemia detection in order to improve the reliability of the detection.

What is claimed is:

1. An implantable heart stimulator comprising a pulse generator which emits stimulation pulses and an electrode lead adapted to deliver said stimulation pulse to cardiac tissue, control means for controlling delivery of said stimulation pulses at a stimulation rate and an ischemia detector, said control means being connected to said ischemia detector for reducing the stimulation rate in response to a detection of ischemia.

2. Heart stimulator according to claim 1, wherein said control means inhibit each nth stimulation pulse in response to the detection of ischemia, where n=is any integer in a range from 8 to 2.

3. Heart stimulator according to claim 1, wherein said control means uniformly reduce the stimulation rate in response to the detection of ischemia.

4. Heart stimulator according to claim 1, wherein said control means shift the stimulation rate to a predetermined lower value in response to the detection of ischemia.

5. Heart stimulator according to claim 1 wherein said control means reduce the stimulation rate as a function of a detected degree of ischemia.

6. Heart stimulator according to claim 1 wherein said ischemia detector comprises an ischemia analyzer for detecting ischemia by analysis of recorded signals selected from the group consisting of IEGMs and ECGs.

7. Heart stimulator according to claim 6, wherein said ischemia analyzer detects ischemia by analysis of a level of ST segments and T-waves in said recorded signals.

8. Heart stimulator according to claim 6, wherein said ischemia analyzer determines heart rate variability from said recorded signals.

9. Heart stimulator according to claim 6, wherein said control means modulate the stimulation rate.

10. Heart stimulator according to claim 1 wherein said ischemia detector comprises a lead bending sensor located at a distal end portion of said electrode lead.

11. Heart stimulator according to claim 1 wherein said ischemia detector comprises means for measuring an AC impedance in a ventricle.

12. Heart stimulator according to claim 1 wherein said ischemia detector comprises means for measuring sound absorption in heart tissue.

13. Heart stimulator according to claim 1 wherein said ischemia detector comprises means for measuring a difference between systolic and diastolic pressures and for comparing said difference obtained from one heartbeat to said difference obtained from a next heartbeat.

14. Heart stimulator according to claim 1 wherein said ischemia detector comprises a flow sensor which identifies cardiac output.

15. Heart stimulator according to claim 1 further comprising an alerting unit activated by the ischemia detector in response to detected ischemia for alerting a subject.

16. Heart stimulator according so claim 15, wherein said alerting unit is activated by said control means when the stimulation rate is reduced.

17. Heart stimulator according to claim 4, wherein said control means includes means for varying said stimulation rate dependent on a sensed workload of a subject, said means for varying the stimulation rate setting the stimulation rate at a workload-responsive stimulation rate in an absence of ischemia, and wherein said control means shifts said stimulation rate to a base rate below said workload-responsive stimulation rate upon a detection of ischemia.

* * * * *